United States Patent [19]

Walling et al.

[11] Patent Number: 5,164,504

[45] Date of Patent: Nov. 17, 1992

[54] HAPTENS, TRACERS, IMMUNOGENS AND ANTIBODIES FOR IMMUNOASSAYS FOR COTININE DERIVATIVES

[75] Inventors: John A. Walling, Round Lake Beach; Hsiang-Yun Hu, Libertyville; Barbara E. Hasz, Park Ridge, all of Ill.

[73] Assignee: Abbott Laboratories, Abbott Park, Ill.

[21] Appl. No.: 641,840

[22] Filed: Jan. 16, 1991

[51] Int. Cl.$^5$ .................. C07D 401/04; C07D 401/14; C07K 3/06; G01N 33/543
[52] U.S. Cl. .................................... 546/281; 546/269; 544/212; 436/518; 530/363; 530/389.8
[58] Field of Search ........................................ 546/281

[56] References Cited

PUBLICATIONS

"Nicotine and Its Metabolites. Radioimmunoassays for Nicotine and Cotinine," by J. J. Langone et al., *Biochemistry*, vol. 12, No. 24, pp. 5025–5030 (1973).

Japanese Patent Applications, Publication Nos. 61-126083 and 61-126084, both to Shibagaki et al. (Japan Tobacco Inc.).

"Nicotine Enzyme Immunoassay," by A. Castro et al., *Research Communications in Chemical Pathology and Pharmacology*, vol. 51, No. 3, pp. 393–404, Mar. 1986.

Chemical Abstract, CA90(7):55278k of Japanese Patent No. 53,31213[78/31213], "Artificial nicotine antigens" to Einosuke Tamaki et al. (Japan Tobacco and Salt Public Corp.).

"Single-reagent polarisation fluoroimmunoassay for cotinine (a nicotine metabolite) in urine," by M. C. Hansel et al., *Ann. Clin. Biochem*, 23:596–602 (1986).

Chemical Abstract, CA83(9):72817h, "Radioimmunoassay of nicotine," to Matsukura et al., *Biochem. Biophys. Res. Commun.*, 64(2), 574–580 (1975).

Chemical Abstract, CA84(3):15593d, "Nicotine antibody production. Comparison of two nicotine conjugates in different animal species," by A. Castro et al. *Biochem. Biophys. Res. Commun.*, 67(2), 583–589 (1975).

*Primary Examiner*—Alan L. Rotman
*Attorney, Agent, or Firm*—Thomas M. Breininger

[57] ABSTRACT

Disclosed is a substantially optically pure hapten, useful in an immunoassay for cotinine. The hapten corresponds to a specified structural formula (I). In formula (I) X is a straight or branched chain, saturated or unsaturated, divalent radical covalently bonded to a pyridyl ring at the number 2-, 4-, 5- or 6-position. The divalent radical, X, has from 1 to 10 carbon atoms wherein the chain of the divalent radical optionally may contain 1 or 2 hetero atoms selected from members of the group consisting of S, O and NZ in which Z represents a $C_1$ to $C_3$ alkyl group. In formula (I), n=1 or 0, and Q is a functional group selected from —COOH, —$NH_2$ (provided that n does not equal 0), —C(O)$NHNH_2$, —O(-CO)Cl, —CHO, —NCS or —NCO.

Also disclosed is an immunogen derived from the hapten as well as an antibody raised in response to an immunogen derived from the hapten.

Also disclosed is a fluorescent tracer derived from a substantially optically pure compound corresponding to the hapten, the tracer being useful in an immunoassay for cotinine.

Also disclosed is an improved immunoassay for determining cotinine in a biological sample involving a step of contacting the sample with antibodies raised in response to the immunogen. Also disclosed is a fluorescence polarization immunoassay (FPIA) for determining cotinine involving a step of contacting the sample with antibodies raised in response to the immunogen, and/or involving a step of contacting the sample with a fluorescent tracer.

6 Claims, No Drawings

HAPTENS, TRACERS, IMMUNOGENS AND ANTIBODIES FOR IMMUNOASSAYS FOR COTININE DERIVATIVES

BACKGROUND OF THE INVENTION

1. Technical Field

The present invention is directed to reagents and methods for performing an immunoassay, particularly a fluorescence polarization immunoassay (FPIA), to determine the presence and/or amount of cotinine in samples, particularly aqueous, fluid biological samples such as urine, blood serum or blood plasma, to a method of making the reagents, and to an immunoassay based on the reagents. More particularly the invention is directed to new haptens, immunogens prepared from the haptens, antibodies raised against the haptens and immunoassays which utilize reagents and methods of the invention.

2. Background

It is believed that a dose-response relationship exists between the number of cigarettes smoked and the risk of developing diseases related to smoking. Insurance companies, surgeons and forensic scientists have shown interest in ways of distinguishing between smokers and non-smokers. Some previous ways have involved the measurement of nicotine and cotinine (a metabolite of nicotine) in biological fluids. Generally, the measurement of urinary cotinine is preferred because (1) in the human body, cotinine is naturally derived only from the metabolism of nicotine, (2) urine is more convenient to collect than blood, (3) cotinine has a half-life of between about 7 and 40 hours, whereas the half-life of nicotine is less than about 30 minutes, and (4) the excretion of cotinine is not as dependent on urinary pH as is nicotine.

The present invention is related to immunoassays, particularly competitive immunoassays, involving reagents and techniques particularly suitable for determining the presence and/or amount of cotinine in biological fluids. The present invention can provide, among others, an advantage of allowing for the determination of the amount of cotinine with minimization of interference from other metabolites of nicotine. The present invention is in part based on new, substantially optically pure haptens, which can be utilized in the preparation of immunogens and/or tracers suitable for use in immunoassays.

3. Background Art

Langone et. al. in *Biochemistry*, 12(24), pages 5025–5030 (1973), describe the use of racemic 3'-hydroxymethylnicotine and 4'-carboxycotinine as haptens in a radioimmunoassay (RIA) for nicotine and cotinine respectively. However, these provide major drawbacks for immunoassays because of the lack of optical activity of these haptens, and possibly because of the positioning of the linking arm in the case of the cotinine hapten. Racemic haptens ultimately lead to antisera wherein no discrimination between optical antipodes is possible and often results in higher levels of interference.

Japanese Patent Applications, Publication Numbers 61-126083 and 61-126084 are directed to the preparation of 4-aminocotinine and 4-aminonicotine and mention possible utility of these compounds as haptens for immunoassays. While these publications suggest that optical purity is maintained during their preparation according to procedures described in these publications, the synthetic sequences are cumbersome. Additionally, because these derivatives are 4-aminopyridines, their efficacy as true haptens for immunoassays is believed to be severely limited because of their poor nucleophilicity at the amino group and the attendant difficulty in attaching "linking arms" for eventual protein conjugation.

*Res. Commun. Chem. Pathol. Pharmacol.*, 51(3), 393–404 describes the use of 6-aminonicotine. However, as in the work described in *Biochemistry*, 12(24), pages 5025–5030 (1973), supra, the material described is racemic.

Japanese Patent Number 53/31213 is directed to the use of 4-, 5-, or 6-para-aminobenzamidonicotine derivatives as haptens which are bound to protein through a diazonium linkage. However, the parent aminonicotine used to prepare such materials is racemic. It is also important to point out that antisera raised against compounds having such rigid and heteroatom-containing linking arms have a higher probability of "bridge antibody" production thus lowering the specificity of the derived immunoassay in general.

SUMMARY OF THE INVENTION

The invention provides for a substantially optically pure hapten, useful in an immunoassay for cotinine. Cotinine is alternatively known as N-methyl-2-(3-pyridyl)-5-pyrrolidone or 1-methyl-5-(3-pyridinyl)-2-pyrrolidinone and occurs as a metabolite of nicotine in fluids of the body, e.g., urine, in the levorotatory (1 or -) enantiomeric form. The hapten of the invention corresponds to the structural formula:

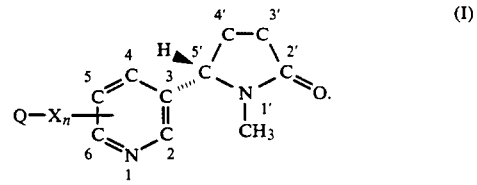

In formula (I) X is a straight or branched chain, saturated, divalent radical having 1 to 10 carbon atoms or an ehtylenically unsaturated divalent radical having 2 to 10 carbon atoms covalently bonded to the pyridyl ring at the number 2-, 4-, 5- or 6-position. The divalent radical, X, is optionally substituted with 1 or 2 hetero atoms selected from members of the group consisting of S, O and NZ in which Z represents a $C_1$ to $C_3$ alkyl group. In formula (I), n=1 or 0, and Q is a functional group selected from —COOH, —NH$_2$ (provided that n does not equal 0), —C(O)NHNH$_2$, —O(CO)Cl, —CHO, —NCS or —NCO. For simplicity, particularly in the working examples infra, compounds corresponding to formula (I) can be alternatively named as derivatives of cotinine. Thus, for example, the compound of the invention prepared in Example 1 having a 2-carboxyethyl group attached at the 6 position of the pyridyl ring is named (s)-(−)-6-(2-carboxyethyl)cotinine and is the levorotatory enantiomer.

The invention also provides for an immunogen derived from a hapten of the invention.

The invention also provides for an antibody raised in response to an immunogen derived from a hapten of the invention.

The invention also provides for a fluorescent tracer derived from a substantially optically pure compound of the invention, the tracer being useful in an immunoassay for cotinine. The substantially optically pure compound corresponds to the hapten defined in formula (I).

The invention also provides for an improved immunoassay for determining the presence or amount of cotinine in a biological sample. The improved immunoassay comprises a step of contacting the sample with antibodies raised in response to an immunogen of the invention. Moreover, the invention provides for a fluorescence polarization immunoassay (FPIA) for determining the presence or amount of cotinine in a biological sample. The FPIA comprises a step of contacting the sample with antibodies raised in response to an immunogen of the invention, and/or comprises a step of contacting the sample with a fluorescent tracer of the invention.

DETAILED DESCRIPTION OF THE INVENTION

A hapten of the invention is substantially optically pure, and is particularly useful in an immunoassay for cotinine, a metabolite of nicotine. As used herein, the phrase "substantially optically pure" means that the product hapten contains less than or equal to 20 percent, preferably less than or equal to 10 percent, and most preferably less than or equal to 5 percent, by weight of the dextrorotatory (d or +) enantiomer of the hapten based on the sum by weight of the dextrorotary and levorotatory (l or −) enantiomers. A hapten of the invention corresponds to the formula (I):

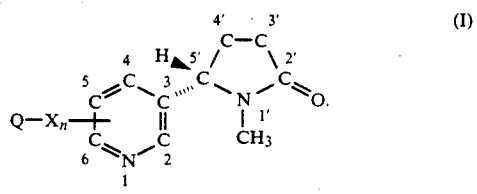

In formula (I), X represents a divalent radical which is covalently bonded to the pyridyl ring shown on the left side of the structural formula (I). The divalent radical, X, may be a straight or branched chain radical, a straight chain radical being preferred. The divalent radical, X, may be saturated or ethylenically unsaturated. The divalent radical, X, is covalently bonded to the pyridyl ring at the number 2-, 4-, 5- or 6-position of the pyridyl ring shown in formula (I). Preferably, the divalent radical, X, is bonded to the pyridyl ring at the number 4-, 5- or 6-position. It has been found that fluorescence polarization immunoassays performed utilizing antisera raised from immunogens prepared from haptens of the invention can provide a particularly high specificity for cotinine and an especially low cross-reactivity for other metabolites of nicotine.

In formula (I), the divalent radical, X, has from 1 to 10 carbon atoms (including any from the branches of a branched chain structure). Optionally, the chain or backbone (as distinguished from any branches) of the divalent radical may contain 1 or 2 hetero atoms selected from members of the group consisting of S, O and N, provided that if N is so included it is in the form of NZ in which Z represents a $C_1$ to $C_3$ alkyl group. In some preferred embodiments of the invention, the divalent radical, X, is a $C_1$ to $C_8$ alkylene group, typically X is —$CH_2CH_2$—.

The subscript, n, on X in structural formula (I) can equal either 1 or zero, provided that when Q is —$NH_2$, n=1. Of course, when n=0 the moiety Q is directly bonded to the pyridyl ring at the number 2-, 4-, 5- or 6-position, preferably at the number 4-, 5- or 6-position, and typically at the number 4- or 6-position of the pyridyl ring.

In formula (I), Q represents a functional group suitable for utilization, for example, in attaching an antigenicity-conferring moiety to the hapten, for example, by reaction directly, or via an intermediate step, with a co-reactive functional group from an antigenicity-conferring carrier. Examples of functional groups suitable for Q include: —COOH, —$NH_2$, —C(O)NHNH$_2$, —O(CO)Cl, —CHO, —NCS and —NCO. In a preferred embodiment of the invention Q is carboxyl, the preparation of which is illustrated, for example, in the working examples infra.

Haptens of the invention can be prepared as follows. Typically, the optically active 2-, 4- and 6-substituted cotinine derivatives (haptens) of the present invention are prepared by the reaction of a suitably functionalized organometallic reagent with cotinine in the presence of a suitable acyl halide derivative. The N-acyl dihydrocotinine derivatives thus obtained are reacted with a suitable oxidizing agent which affects the removal of the N-acyl group with concomitant rearomatization of the pyridine ring moiety of cotinine. The overall linkage of the alkylene group containing additional functionality to the 2-, 4- and 6-positions of cotinine in this manner is central to the obtention of haptenic cotinine derivatives of substantial optical activity. The products thus obtained above are manipulated by methods common to those skilled in the art to haptenic materials described herein.

The acyl halide derivatives described above may be aliphatic acid chlorides or bromides such as acetyl chloride, pivaloyl chloride and the like. Acid halides derived from aromatic acids show lesser utility. Alternatively, chloroformate derivatives of aromatic and aliphatic alcohols may be used with the chloroformate derivatives of aliphatic alcohols being preferable.

The organometallic compounds utilized in the present invention are readily prepared by those skilled in the art and have as additional functionality: ester, nitrile, ether or olefinic groups at a position distal to the metallic center as described in the examples. The oxidizing agents useful for the conversion of the intermediate N-acyldihydrocotinine derivatives to functionalized cotinine derivatives include sulfur, quinone derivatives, silver salts and other inorganic salts of iron and the like which are generally known to those skilled in the art. Of particular utility for the oxidation of the intermediate N-acyldihydrocotinine derivatives is ammonium cerium(IV)nitrate. This form of cerium(IV) is provided by way of example and other salts such as ammonium cerium(IV)sulfate and the like may also be used.

The 5-substituted cotinine derivatives of the present invention are prepared by reaction of a suitable formylation reagent with N-acyldihydropyridine derivatives obtained via the hydride reduction of cotinine in the presence of acyl halide derivatives. Reagents suitable for formylation are known to those skilled in the art and include, but are not limited to, dimethylformamide/phosphorous oxychloride an dimethylformamide/phosgene. The 5-formyldihydrocotinine derivatives thus obtained are oxidized to cotinine derivatives by the reagents outlined above. The products thus obtained are manipulated to haptenic cotinine derivatives by methods and techniques known to those skilled in the art.

Covalent linkage of the haptenic materials described herein to antigenicity-conferring materials can be accomplished by methods well known in the art, the choice of which will be dictated by the nature of the linking functionality in the cotinine derivative and the carrier chosen for the linkage.

An immunogen of the invention is derived from a substantially optically pure hapten of the invention. An immunogen of the invention is particularly useful in an immunoassay for cotinine. The immunogen corresponds to the formula:

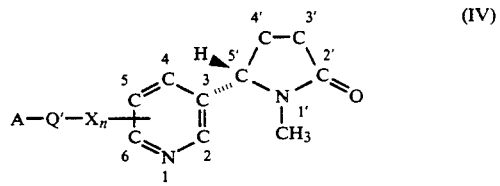

wherein X is as defined for the hapten corresponding to formula (I) above and n=1 or 0, preferably 1. In structural formula (IV), Q is a divalent radical selected from —NHC(O)—, —OC(O)NH—, —NH=CH—, —NH$_2$=CH—, —NHCH$_2$—, —NHC(S)NH—, and NHC(O)NH—, —NHNHC(O)—, provided that when Q' is —OC(O)NH—, —NHC(S)NH— or —NHC(O)NH—, n=1. It is to be understood that wherever in the specification and claims herein, a divalent moiety for linking two other structures together is specified, e.g., —NHC(O)— as Q' for linking A and $X_n$, the left hand portion of the divalent moiety is attached to the structure on the left and the right hand portion is attached to the structure on the right (i.e, for this example A—NHC(O)—$X_n$).

In formula (IV), A is an antigenicity-conferring carrier moiety. When n=1, Q' serves to link the antigenicity-conferring carrier moiety, A, to the divalent radical X. When n=0, Q' serves to link the antigenicity-conferring carrier moiety, A, directly to the pyridyl ring of the hapten at the 2-, 4-, 5- or 6-position, preferably at the 4-, 5- or 6-position, and typically at the 4- or 6-position. The antigenicity-conferring carrier moiety, A, can be selected from a wide variety of antigenicity-conferring carrier moieties. As can be appreciated from formula (IV), the moiety A represents the residue of an antigenicity-conferring carrier bound via Q' to the haptenic portion of the immunogen of formula (IV).

Typically, the antigenicity-conferring carrier moiety, A, is provided by reacting the functional group Q of a hapten corresponding to formula (I) with a co-reactive functional group of an antigenicity-conferring carrier such as, for example, a naturally occurring or synthetic poly(amino acid) by generally known preparative techniques. Typically, in preferred embodiments of the invention, the naturally occurring poly(amino acid), bovine serum albumin (BSA), is utilized as the, antigenicity-conferring carrier to provide the moiety, A, in structural formula (IV), but it is to be understood that other protein carriers can be utilized, including for example, albumins and serum proteins such as globulins, lipoproteins, ocular lens proteins, and the like. Some illustrative antigenicity-conferring protein carriers include bovine serum albumin, keyhole limpet hemocyanin, egg ovalbumin, bovine gamma globulin, thyroxine binding globulin, etc. Alternatively, synthetic poly(amino acids) can be utilized such as polylysine, etc.

For example, as illustrated more specifically in the examples below, a hapten in which Q of formula (I) is carboxyl, is coupled to bovine serum albumin, preferably under conditions normally used to form amide bonds which conditions are well known to those skilled in the art, by utilizing as the coupling agent, for example, a carbodiimide, especially a water soluble carbodiimide such as 1-ethyl-3-(3-dimethylaminopropyl) carbodiimide (EDC) or 1-cyclohexyl-3-(2-morpholinoethyl)-carbodiimide metho-p-toluenesulfonate. The same reagents can be used in the case where Q of the hapten is a —NH$_2$ group or —C(O)NHNH$_2$ group, in which case an amide bond is formed with a carboxyl group on the bovine serum albumin. When Q of the hapten is —NCO, —NCS or —O(CO)Cl, the immunogen can be prepared, for example, by mixing the poly(amino acid) directly with the hapten. When Q of the hapten is —CHO, the aldehyde can be reductively aminated to a corresponding amine functional group. Other transformations of the aldehyde into useful haptens are obvious to one skilled in the art.

Antibodies of the present invention are prepared by developing an immune response in animals to immunogens of the invention. The immunogen is administered to animals such as rabbits, mice, rats, sheep or cows by a series of injections according to techniques generally known in the art. An antibody, according to the present invention, is raised in response to an immunogen of the invention which is derived from a substantially optically pure hapten of the invention. Both polyclonal and monoclonal antibodies recognize specific epitopes on an immunogen, and, while typically polyclonal antibodies have been utilized in the present invention, both may be suitable. Polyclonal antibodies consist of a mixture of multiple antibodies, each recognizing a specific epitope, whereas monoclonal antibodies are produced by cells secreting a single antibody recognizing a specific epitope. Techniques for preparing polyclonal antibodies generally are well known in the art. Monoclonal antibodies may be prepared by injecting animals, such as mice or rats, intraperitoneally, subcutaneously, intravenously, or in some other manner, with an antigen, namely an immunogen corresponding to formula (IV) above, to elicit an immune response in the animals (namely, the production of antibodies which are specific for the antigen). Sera from the animals are drawn, and the sera are tested to determine the titer of antibody in the sera (to determine whether or not the animal elicited the desired immune response, and to what extent). Those animals in which the desired immune response has been produced are permitted to rest for approximately two to three months. After this two-month to three-month period of time, and approximately t days prior to the anticipated fusion of B-lymphocyte cells (cells which, upon antibody, and which are also referred to as B cells) with myeloma cells (tumor cells), a boost injection of the antigen is administered to these animals. B-lymphocyte cells are then removed from the spleens of these animals by standard procedures, and the B-lymphocyte cells are then fused with myeloma fusion partners according to standard procedures, such as those described in Kohler and Milstein, "Continuous Culture of Fused Cells Secreting Antibody of Predefined Specificity," Nature, 256, 495 (1975). The B-lymphocyte-myeloma fusions are then plated in multiwell tissue culture plates containing HAT media, or other suitable media. The resulting cultures are fed with HT media, or other suitable media, and fetal bovine serum or calf bovine serum on or about the fifth and seventh days after the fusion of the cells and then tested on or about the tenth day after the fusion for the presence of antibody which is specific for the antigen. Specific desirable hybrids are then cloned by limiting dilution. (Hybrid cells are diluted in differing amounts of HT media, or other suitable media, and plated out in tissue culture plates in order to isolate a single desired clone.) Established clones are then retested for specificity to a broader panel of cross reactants.

The amount of the resulting monoclonal antibodies produced by a desired clone can then be scaled up to produce a sufficient quantity of antibody for purification in either: (1) tissue culture (by expanding the number of cells in tissue culture, or HT media); or (2) mice for ascites. The monoclonal antibodies can be scaled up in mice by injecting hybrid cells into the abdominal cavity of mice and allowing the cells to grow (usually for about 7 days). The ascites is harvested from the mice by sacrificing the mice, collecting the ascites fluid, and purifying the ascites fluid. BALB/c mice are the most common strain of laboratory mouse used for this process, and they can be obtained from any mouse vendor. Pristane, should be injected into the mice to stimulate their immune systems to produce B and T cells (about two or three weeks before the hybrid cells are injected into the mice) which serve as a feeder layer for the clone cells that are injected into the mice. This is performed to provide a suitable environment in which the hybrid cells can grow.

The invention also provides for improved immunoassays for determining the presence or amount of cotinine in biological samples. An improved immunoassay of the invention includes (comprises) a step of contacting the sample to be determined with antibodies raised in response to an immunogen of the invention. It is contemplated that any immunoassays for cotinine utilizing haptens, immunogens, and/or antibodies raised against immunogens, according to the invention, are within the scope of the present invention. Examples of immunoassays include radioimmunoassays (RIAs), enzyme immunoassay (EIAs), enzyme linked immunosorbent assays (ELISAs) and fluorescent polarization immunoassays (FPIAs). In a fluorescent polarization immunoassay (FPIA), a fluorescent tracer of the invention may be utilized either with or without utilization of antibodies raised in response to an immunogen of the invention.

A fluorescent tracer of the invention can be thought of as being derived from a substantially optically pure compound corresponding to a hapten of the invention. A tracer of the invention is useful in an immunoassay for cotinine and corresponds to the formula:

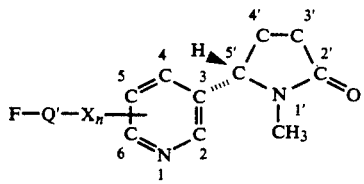 (V)

wherein X is as defined for the hapten corresponding to formula (I) above, n=1 or 0, preferably 1. Q' in formula (V) is a divalent radical selected from —NHC(O)—, —OC(O)NH—, —C(O)NHNH—, —NHC(S)NH— and —NHC(O)NH—, provided that when Q' is —OC(O)NH—, —NHC(S)NH— or —NHC(O)NH—, n=1.

In formula (V), F is a fluorescence-conferring moiety. When n=1, Q' serves to link the fluorescence-conferring moiety, F, to the divalent radical X. When n=0, Q' serves to link the fluorescence-conferring moiety, F, directly to the pyridyl ring at the 2-, 4-, 5- or 6-position, preferably at the 4-, 5- or 6-position, and typically at the 4- or 6-position. The fluorescence-conferring moiety, F, can be selected from a wide variety of fluorescence-conferring moieties. As can be appreciated from formula (V), the moiety F represents the monovalent residue of a fluorescence-conferring compound bound via Q' to the remainder of the tracer, either through X when n=1, or directly to the pyridyl ring when n=0. In preferred embodiments of the invention, the fluorescence-conferring moiety of the fluorescent tracer is a monovalent residue of fluorescein or a monovalent residue of a fluorescein derivative. By way of example, any of the following fluorescein derivatives can be used:

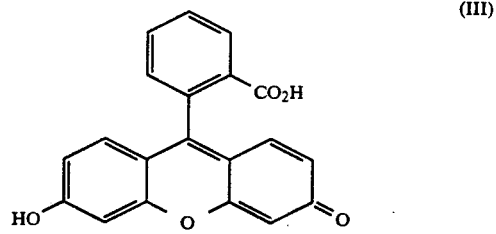

| Fl-CH2NH2 | aminomethylfluorescein |
| Fl-NH2 | fluorescein amine |
| Fl-CO2H | carboxyfluorescein |
| Fl-NHCOCH2I | alpha-iodoacetamidofluorescein |
| | 4,6,-dichloro-1,3,5,-triazin-2-yl amino-fluorescein (DTAF) |
| | 4-chloro-6-methoxy-1,3,5,-triazin-2-ylamino fluorescein |
| Fl-NCS | fluorescein thioisocyanate |

As used above, Fl stands for a fluorescein moiety corresponding to the following formula (III):

(III)

Tracers of the invention generally can be prepared by linking an appropriate fluorescent compound to a hapten of the invention represented by formula (I) above in which Q represents a functional group suitable for utilization in attaching the fluorescent compound to the hapten, for example, by reaction directly, or via an intermediate step, with a co-reactive functional group from the fluorescent compound. Examples of functional groups for the hapten include: —COOH, —NH2 (provided that n does not equal 0), —C(O)NHNH2, —O(CO)Cl, —NCS and —NCO.

Normally, competitive binding immunoassays are utilized according to the method of the invention to determine the presence and/or amount of cotinine in a sample. Typically, competitive binding immunoassays are used for measuring ligands in a test sample. For purposes of this disclosure, a "ligand" is a substance of biological interest (cotinine) to be quantitatively determined by a competitive binding immunoassay technique. The ligand competes with a labeled reagent (a "ligand analog" or "tracer") for a limited number of ligand binding sites on antibodies specific to the ligand and ligand analog (herein, antibodies prepared in response to an immunogen of the invention). The concentration of ligand in the sample determines the amount of ligand analog which binds to the antibody, and the amount of ligand analog that will bind to the antibody is inversely proportional to the concentration of ligand in the sample, because the ligand and the ligand analog each bind to the antibody in proportion to their respective concentrations.

In one embodiment of the invention, fluorescence polarization immunoassay (FPIA) techniques are utilized for determining the amount of tracer-antibody conjugate produced in a competitive binding immunoassay. Such procedures are based on the principle that a fluorescent labeled compound, when excited by plane polarized light, will emit fluorescence having a degree of polarization inversely related to its rate of rotation, Accordingly, when a tracer-antibody conjugate having a fluorescent label is excited with plane polarized light, the emitted light remains highly polarized because the fluorophore is constrained from rotating between the time that light is absorbed and emitted. In contrast, when an unbound tracer is excited by plane polarized light, its rotation is much faster than the corresponding tracer-antibody conjugate and the molecules become more randomly oriented. As a result, the light emitted from the unbound tracer molecules is depolarized.

More specifically, a preferred FPIA method of the present invention for determining the presence or amount of cotinine in a sample comprises the steps of: (a) contacting a sample with: (1) an antiserum containing monoclonal or polyclonal, typically polyclonal, antibodies which have been raised in response to an immunogen of the invention; and (2) a fluorescent tracer of the invention, the fluorescent tracer being capable of producing a detectable fluorescence polarization response to the presence of the antiserum; (b) passing plane polarized light through the resulting solution from step (a) to obtain a fluorescence polarization response; and (c) detecting the fluorescence polarization response of the solution of step (b) as a measure of the presence or amount of cotinine in the sample.

By maintaining constant the concentration of fluorescent tracer and antibody, the ratio of cotinine-antibody complex to fluorescent tracer-antibody complex that is formed is directly proportional to the amount of cotinine in the sample. Upon exciting the mixture with linearly polarized light and measuring the polarization (in units of millipolarization) of the fluorescence emitted by a fluorescent tracer and a fluorescent tracer-antibody complex, one is able to quantitatively determine the amount or qualitatively determine the presence of cotinine in the sample.

The results can be quantified in terms of net millipolarization units and span (in millipolarization units). The measurement of net millipolarization units indicates the maximum polarization when a maximum amount of the fluorescent tracer is bound to the antibody, in the absence of any cotinine. The higher the net millipolarization units, the better the binding of the tracer to the antibody. The assay span is the difference between the net millipolarization values obtained when the maximum amount of tracer is bound in the absence of any cotinine and the net millipolarization obtained when a specific amount of cotinine is present in the sample. A larger span allows for more millipolarization units to be placed between each of the calibrators of the standard curve generated for the assay, thereby providing better assay precision which, in turn, results in a better numerical analysis of the data obtained. It is important to note that the span varies depending on the sample size used which, in turn, may alter the preferred combination.

Fluorescent tracers of the present invention are substantially optically pure. These tracers have the particular advantage in instances where antisera based on polyclonal antibodies are utilized. Because cotinine is essentially optically pure in the body, the use of tracers which are substantially optically pure in combination with antibodies derived from substantially optically pure immunogens have been found to allow for enhanced signal attenuation across the chosen dynamic range in a cotinine assay utilizing FPIA techniques. One resultant advantage is that FPIA assays of the present invention can achieve sensitivities of the order of 50 nanograms/milliter of cotinine in the sample as compared to disadvantageously lower sensitivites from prior art FPIA assays for cotinine.

Some significant features of the most preferred combination of fluorescent tracer of the present invention and immunogen of the present invention, include: (1) the high degree of specificity of the antibodies, generated in response to the immunogen, for cotinine, and (2) minimal cross reactivity of these antibodies to other metabolites of nicotine.

The pH at which an FPIA method of the present invention is practiced must be sufficient to allow the fluorescein moiety of the fluorescent tracer to exist in its open form. The pH may range from about 3 to 12, more usually in the range of from about 5 to 10, most preferably from about 6 to 9. Various buffers may be used to achieve and maintain the pH during the FPIA procedure. Representative buffers include borate, phosphate, carbonate, tris, barbital, citrate and the like. The particular buffer employed is not critical to the present invention, but the tris, phosphate citrate buffers are preferred. The cation portion of the buffer will generally determine the cation portion of the tracer salt in solution.

Riboflavin binding protein (RBP) is added to the sample or to one or more of the assay reagents to bind any riboflavin present in the sample into RBP-riboflavin complexes, thus eliminating potential fluorescence interference. RBP is a protein of approximately 32,000 M.W. which is isolated from egg whites. Upon isolation from the egg, each molecule of RBP contains one molecule of riboflavin. This, the holoprotein form of RBP, must be converted to the apoprotein form by dialysis, under acidic conditions, to remove the bound riboflavin. The RBP apoprotein utilized in the present invention is commercially available from Sigma Chemical Company, St. Louis, Mo. The amount used is not critical, provided a sufficient quantity is used to bind all free riboflavin in the sample.

A fluorescent polarization immunoassay of the present invention is a "homogeneous assay," which means that the end polarization readings are taken from a solution in which bound tracer is not separated from unbound tracer. This is a distinct advantage over heterogeneous immunoassay procedures, such as those where the bound tracer must be separated from the unbound tracer before a reading can be taken.

The reagents for the fluorescence polarization assay of the present invention comprise: (1) polyclonal or monoclonal, typically polyclonal, antibodies, for cotinine; and (2) fluorescent tracer reagent.

Additionally, largely conventional solutions including a pre-treatment solution, a dilution buffer, cotinine calibrators and cotinine controls are desirably prepared. Typical solutions of these reagents, some of which are described below, are commercially available in assay "kits" from Abbott Laboratories, Abbott Park, Ill.

All percentages expressed herein are weight/volume unless otherwise indicated. The preferred reagents, calibrators and controls for a preferred fluorescence polarization immunoassay of the present invention can be found in Example 8 infra.

The preferred FPIA procedure is especially designed to be used in conjunction with the Abbott $TD_x$ ® Clinical Analyzer or the Abbott $AD_x$ ® Drugs of Abuse System, both of which are available from Abbott Laboratories, Abbott Park, Ill. The calibrators, controls, or unknown samples are pipetted directly into the sample well of the $TD_x$ ® sample cartridge. One of the advantages of this procedure is that the sample does not require any special preparation. The assay procedure from this point is fully automated.

If a manual assay is being performed, the sample is mixed with the pretreatment solution in dilution buffer and a background reading is taken. The fluorescence tracer is then mixed with the assay. The antibody is then finally mixed into the test solution. After incubation, a fluorescence polarization reading is taken.

The fluorescence polarization value of each calibrator, control or sample is determined and is printed on the output tape of an instrument, such as the Abbott $TD_x$ ® Analyzer or $AD_x$ ® System. A standard curve is generated in the instrument by plotting the polarization of each calibrator versus its concentration using a nonlinear regression analysis. The concentration of each control or sample is read off of the stored calibration curve and printed on the output tape.

With respect to the foregoing preferred procedure, it should be noted that the tracer, antibody, pretreatment solution, wash solution, calibrators and controls should be stored between about 2° C. and about 8° C. while the dilution buffer should be stored at ambient temperature. A standard curve and controls should be run every two weeks, with each calibrator and control run in duplicate. All samples can be run in duplicate.

The following examples are provided to further illustrate embodiments of the invention and should not be construed as a limitation on the scope of the invention.

The following general experimental procedures were utilized in the preparation of the haptens of the following examples.

All reactions were carried out under an atmosphere of dry Ar unless otherwise noted. Optical rotations were recorded on a Perkin-Elmer model 241 polarimeter using a 0.1 dm cell and the sodium D-line as a spectral source. Proton NMR spectra were recorded on either a Chemmagnetics model A-200 (200 MHz) or General Electrical model QE-300 (300 MHz) spectrometer. Proton NMR recorded in $CDCl_3$ used tetramethylsilane as an internal reference. The following abbreviations are used to designate the multiplicity of NMR signals: s, singlet; d, doublet; t, triplet; q, quartet; bs, broad singlet.

Solvents for chromatography were high performance liquid chromatography (HPLC) grade and were used without additional purification. Anhydrous tetrahydrofuran (THF) was distilled from Na / benzophenone ketyl under Argon just prior to use. Anhydrous methylene chloride was distilled from calcium hydride. All other chemicals were used as received from the vendors. All solvents used to extract aqueous solutions were dried with magnesium sulfate and evaporated on a rotary evaporator at or below 35° C. Column chromatography was performed on E. Merck silica gel 60, 230-400 mesh ASTM. Analytical thin-layer and preparative layer chromatography was performed on E. Merck precoated silica gel 60 F 254 plates.

Nomenclature for all compounds is based on the numbering system presented in formula (I) infra.

EXAMPLE 1

This example illustrates the preparation of a hapten of the invention, namely, (s)-(−)-6-(2-carboxyethyl)cotinine, corresponding to the following formula (VI).

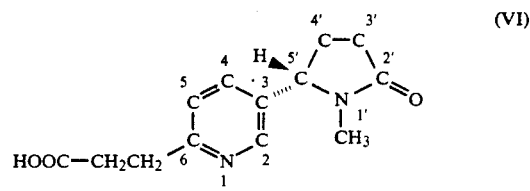

Part (a) A 25 ml round bottomed flask equipped with stir ba and septa was charged with 211 milligrams (mg; 4.0 millimole, mmol) of zinc-copper couple (Zn-Cu) and the flask was flushed with Argon. The couple was suspended in 5.5 milliliters (ml) of dry benzene and 0.35 ml of dry dimethylformamide (DMF) was added. To this stirred suspension was added 600 mg (2.63 mmol) of ethyl 3-iodopropionate, and the mixture was stirred 1 hour at ambient temperature and then heated to 60 degrees C. for 4 hours. The resulting organozinc reagent was cooled to ambient temperature and added dropwise via cannula to a mixture of 404 mg (2.30 mmol) of (−)-cotinine (i.e., levorotatory cotinine) and 0.29 ml (2.30 mmol) oil phenyl chloroformate in 10 ml of benzene. The resulting suspension was stirred for 20 minutes and then treated with 5 ml of 10% by weight aqueous HCl and 10 ml of diethyl ether. The phases were separated and the aqueous phase was extracted with a 5 ml portion of ether. The combined organic extracts were washed sequentially with 10% aqueous HCl, saturated aqueous sodium bicarbonate and dried magnesium sulfate ($MgSO_4$). After filtration and rotary evaporation, 613 mg of a clear oil was obtained.

Part (b) A portion (466 mg) of this crude mixture (from part a immediately above) was dissolved in 20 ml of benzene and 1 ml of glacial acetic and 294 mg (1.30 mmol) of 2,3-dicyanobenzoquinone (DDQ) was added. The reaction mixture was warmed to reflux for 1 hour, then cooled to ambient temperature and cast into 100 ml of cold water. The aqueous phase was made basic to pH 9 with sodium bicarbonate and extracted with two 20 ml portions of 1:1 diethyl ether/ethyl acetate. The product obtained after drying and rotary evaporation was chromatographed on silica gel using methanol/chloroform mixtures to provide 48.7 mg (7.6% by weight) of pure compound corresponding to formula (VII) as a nonmobile oil: TLC (5% methanol/CHCl3) Rf=0.28; 1H NMR (200 MHz, CDCl3) delta 8.40(d, 1H, J=2 Hz), 7.43(dd, 1H, J=8, 2 Hz), 7.23(d, 1H, J=8 Hz), 4.54(m, 1H), 4.13(q, 2H, J=7 Hz), 3.25(t, 2H, J=7 Hz), 2.80(t, 2H, J=7 Hz), 2.66(s, 3H), 2.62–2.38(m, 3H), 1.95–1.75(m, 1H), 1.21(t, 3H, J=j Hz); [alpha]$_D^{25}$ −24.5 (c=0.20 in ethanol).

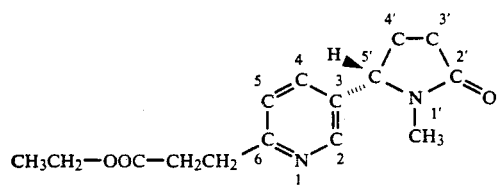

Part (c) To a solution of 48 mg (0.17 mmol) of (VII) in 2 ml of 75% by weight aqueous methanol was added 12 mg (0.51 mmol) of powered lithium hydroxide, and the resulting mixture was stirred 7 hours at ambient temperature and evaporated to dryness. The crude product was chromatographed on silica gel using methanol/chloroform mixtures to provide 29.1 mg (74%) of compound (VI) as a clear colorless glass: [alpha]$_D^{25}$ −15(c=1.32 in methanol). Compound (VI) is a hapten of the invention useful for generation of anti-cotinine antibodies.

EXAMPLE 2

This example illustrates the preparation of compound, namely, (S)-(−)-6-(3-hydroxypropyl)cotinine, which is useful in the preparation of fluorescent tracers of the invention for immunoassays for cotinine. The compound corresponds to the following formula (VIII).

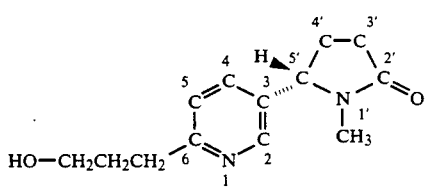

Part (a) To a cold (0° C.) solution of 176.4 mg (1.0 mmol) of (−)-cotinine in 10 ml of tetrahydrofuran (THF) was added 96 microliters (ul) containing 1.0 mmol of ethyl chloroformate, and the resulting white suspension was stirred for 10 minutes at 0° C. The suspension was cooled to −78° C. and treated with 1.32 ml of a 0.77 molar (M) THF solution (1.02 mmol) of 3-butenyl magnesium bromide dropwise over 5 minutes. The reaction mixture was stirred for 30 minutes at −78° C., warmed to ambient temperature and quenched by the addition of 15 ml of ether and 5 ml of water. Workup as per Example 1, part (a) provided 129 mg of a clear colorless oil.

Part (b) The oil obtained from part (a) immediately above was dissolved in 6 ml of acetonitrile, and a solution of 330 mg (0.60 mmol) of ammonium cerium(IV) nitrate (CAN) in 2.0 ml of water was added dropwise with vigorous stirring. After the addition was complete, the mixture was stirred for an additional 5 minutes at ambient temperature, diluted with 20 ml of chloroform and 800 mg (4.16 mmol) of citric acid was added. The mixture was basified with enough saturated aqueous sodium carbonate to yield a final pH of 9, and the phases were separated. The aqueous phase was extracted with a 10 ml portion of chloroform. The organic extracts were combined, washed with water and dried (MgSO4). The residue obtained after filtration and evaporation was chromatographed on silica gel to afford 37 mg of compound corresponding to formula (IX) and 18 mg of compound corresponding to formula (X) as clear nearly colorless oils. For (IX): 1H NMR (300 MHz, CDCl3) delta 8.41 (d, 1H, J=2.5 Hz), 7.42 (dd, 1H, J =8,1, 2.5 Hz), 7.19 (d, 1H, J=8.1 Hz), 5.95–5.81 (m, 2H), 5.11–4.96 (m, 1H), 2.90 (m, 2H), 2.67 (s, 3H), 2.63–2.41 (m, 5H), 1.94–1.82 (m, 1H); For (X): 1H NMR (300 MHz, CDCl3) δ8.46 (d, 1H, J=5.7 Hz), 8.32 (s, 1H), 7.15 (d, 1H, J=5.7 Hz), 5.90–5.76 (m, 1H), 5.11–5.03 (m, 2H), 4.88–4.80 (m, 1H), 2.81–2.35 (m, 10H), 1.92–2.80 (m, 1H); [alpha]$_D^{25}$ −60.4° (c=0.26 in ethanol; MS (EI) m/e 230 (M+) (22%), 215(15%), 201(39%), 188(66%), 173(16%), 158(36%), 98(100%); IR (CDCl3) 1680, 1598, 1400, 1270, 1108 cm$^{-1}$.

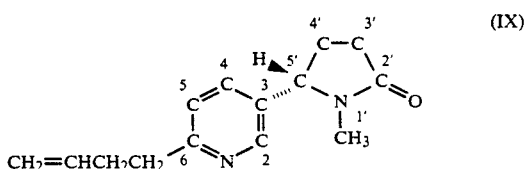

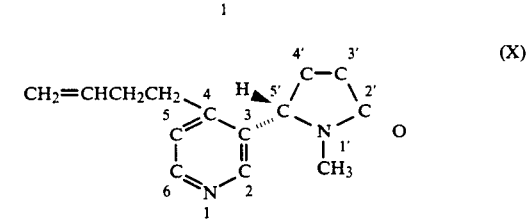

Part (c) Compound (X) obtained above (0.16 mmol) was dissolved in 7.5 ml of methylene chloride and 0.5 ml of ethyl acetate and treated with stirring with 14 microliter (ul) of trifluoroacetic acid. The mixture was cooled to −78° C. and a stream of ozone passed in until the faint blue color of excess ozone could be observed. Argon gas was bubbled in to displace the excess ozone and the mixture was then treated with 0.25 ml (3.4 mmol) of dimethylsulfide. The mixture was allowed to warm to ambient temperature overnight. After aqueous workup, there was obtained the crude aldehyde as an oil.

Part (d) The crude aldehyde of part (c) immediately above was dissolved in 4 ml of methanol and cooled with stirring to 0° C., and the mixture was treated with 25 mg (0.65 mmol) of sodium borohydride. The mixture was slowly warmed to ambient temperature overnight. The excess hydride was destroyed by the addition of 0.5 ml of 5% aqueous hydrochloric acid, brought to pH=10 with saturated aqueous sodium bicarbonate and the product extracted into chloroform (5 ml). After drying, filtration and concentration, 11.5 mg of the crude alcohol was obtained. The product was further purified by chromatography on silica gel using methanol/chloroform mixtures to provide 3.6 mg of highly pure VIII as a clear colorless oil: 1H NMR (300 MHz, CDCl3) delta 8.49 (d, 1H, J=2.4 Hz), 7.47 (dd, 1H, J=7.6, 2.4 Hz), 7.33 (d, 1H, j =7.6 Hz) 4.53 (m 1H), 3.73 (t, 2H, J=6.6 Hz), 3.66 (bs, 1H), 2.99 (t, 1H, J=6.6 Hz), 2.67 (s, 3H), 2.65–2.41 (m, 3H), 2.05–1.94 (m, 2H), 1.92–1.81 (m, 1H).

EXAMPLE 3

This example illustrates the preparation of a preferred hapten of the invention, namely, (S)-(−)-4-(2-carboxyethyl)cotinine, corresponding to the following formula (XI)

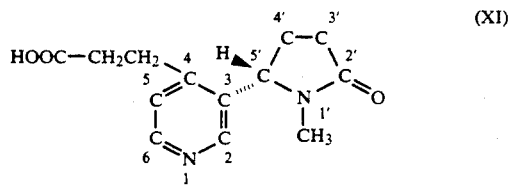

Part (a) To a cold (−20° C.) suspension of 463 mg (2.43 mmol) of cuprous iodide in 8 ml of THF was added dropwise 3.15 ml of a 0.77 M solution (2.43 mmol) of 3-butenyl magnesium bromide. The mixture was stirred for 20 minutes at −20° C., cooled to −78° C., and 0.30 ml (2.43 mmol) of boron trifluoride etherate was added slowly. The resulting grey-brown suspension was transferred via a double-ended needle to a cold (−78° C.) mixture of 364 mg (2.07 mmol) of cotinine and 0.19 ml of ethyl chloroformate in 8 ml of THF. The reaction mixture was warmed to ambient temperature over 1 hour and then worked up as per Example 1, part (a) to provide 285 mg of a crude mixture of addition products.

Part (b) The crude addition products of Example 3, part (a) immediately above were dissolved in 25 ml of acetonitrile. A solution of 1.03 grams (g, 1.8 mmol ) of CAN in 5 ml of water was added dropwise with stirring and the resulting solution was stirred for 10 minutes at ambient temperature. To the pale yellow solution was added 100 mg of sodium bisulfite to destroy the excess CAN and the reaction was worked up per Example 2, part (b). After chromatography, there was obtained 69 mg of pure (X) and 6.8 mg of (IX) (see Example 2 for analytical data on (X) and (IX).

Part (c) A cold (−78° C.) solution of 302 mg (1.31 mmol) of (X) in 30 ml of methylene chloride and 4 ml of methanol was treated with ozone and worked up with dimethylsulfide in a similar fashion as that described in Example 2, part (c). Chromatography of the crude residue provided 286 mg of the pure aldehyde (XII) as a clear colorless oil: $^1$H NMR (300 MHYz, CDCl3) δ9.88 (s, 1H), 8.48 (d, 1h, J=5.2 Hz), 8.31 (bs, 1H), 7.13 (d, 1H, J=5.2 Hz), 4.94–4.86 (m, 1H), 3.08–2.82 (m, 4H, 2.70–2.42 (m, 7H), 1.92 –1.76 (m, 1H). Compound (XII) is a potential cotinine hapten and may be conjugated to a protein carrier via reductive amination procedures common to those skilled in the art.

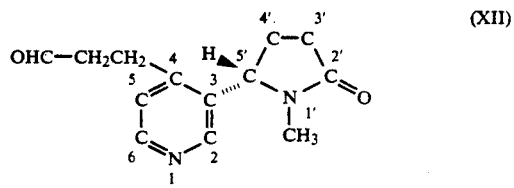

Part (d) The aldehyde prepared in Example 3, part (c) immediately above was dissolved in 1.8 ml of tert- butyl alcohol and 0.42 ml of 2-methyl-2-butene. With vigorous stirring, a solution of 53 mg of sodium chlorate in 0.4 ml of 0.1 M pH=3.5 phosphate buffer was added dropwise and the mixture was stirred for 3 hours. The reaction mixture was concentrated to dryness on a rotary evaporator and the residue chromatographed on silica gel using methanol/chloroform mixtures to afford 76.0 mg of (XI) as a hygroscopic foam: $^1$H NMR (300 MHz, CD$_3$OD ) δ8.38 (d, 1H, J=5.3 Hz), 8.19 (bs, 1H), 7.38 (d, 1H, J=5.3 Hz), 5.08 (m, 1H), 3.05–2.95 (m, 2H), 2.72 (s, 3H), 2.7s (s, 3H), 2.71-2.45 (m, 5H), 1.93–1.80 (m, 1H); MS (DCI, NH$_3$) M++H @m/e=249; [alpha]$_D^{28}$ −76.8° (c=0.25 in ethanol).

EXAMPLE 4

This example illustrates the preparation of a preferred fluorescent tracer of the invention, namely 3-[(−)-4-cotinyl] propionic acid aminomethyl fluorescein amide, which corresponds to formula (XIII).

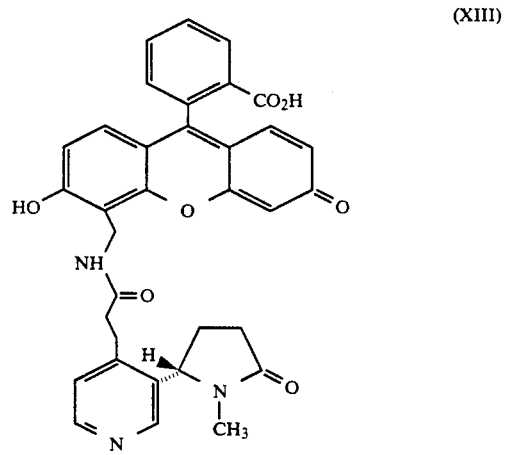

The acid prepared in Example 3, part (d) immediately above, namely, (S)-(−)-4-(2-carboxyethyl)cotinine corresponding to formula (XI), in an amount of 27.2 mg (0.110 mmol) was dissolved in 500 microliters (uL) each of THF, dioxane and N-methylpyrrolidinone (NMP). To this solution was sequentially added 44 mg (0.110 mmol) of 4'-aminomethylfluorescein hydrochloride, 64 uL (0.43 mmol) of triethylamine and 33.5 mg (0.132 mmol) of bis(2-oxo-3-oxazolidinyl)phosphinic chloride (BOP-Cl), and the mixture was stirred for 4 hours at ambient temperature. The mixture was concentrated to near dryness in vacuo and applied to 1.0 mm ×20 cm ×20 cm silica gel plates, and each was developed with 15% methanol in chloroform (2×). The appropriate band was removed from the plate, powdered and the fluorescein derivative eluted from the gel with methanol. The derivative was similarly chromatographed twice more to provide 45 mg of (XIII), the fluorescein derivative depicted in formula (XIII): MS (FAB) yields MH+@594.

EXAMPLE 5

This example illustrates the preparation of a fluorescent tracer of the invention, namely 3-[(−)-6-cotinyl] propionic acid aminomethyl fluorescein amide, which corresponds to formula (XIV).

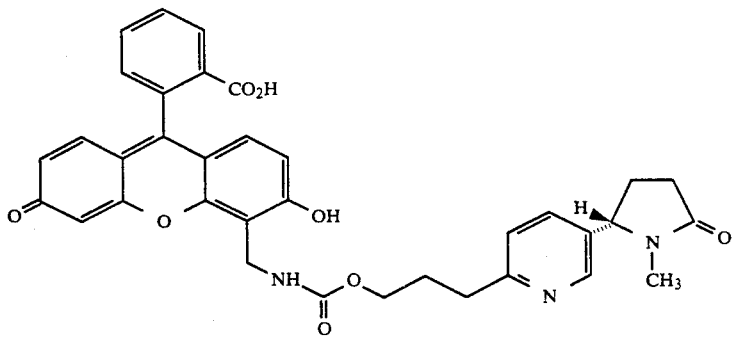
(XIV)

To a solution of 3.6 mg (0.0154 mmol) of alcohol (VIII) (prepared in Example 2, part d above) in 0.15 ml of dry dioxane was added 60 microliters (uL) of a 2.4 M solution of phosgene in benzene, and the resulting mixture was stirred at ambient temperature for 5 minutes. The solvents were removed in vacuo and the residue was dissolved in 0.10 ml of dry dioxane. To this stirred solution was added 4.8 mg (0.012 mmol) of 4'-aminomethylfluorescein, 0.05 ml of NMP and 6.5 uL (0.046 mmol) of triethylamine. The mixture was stirred for 10 minutes and an additional 6.0 uL of triethylamine was added. After stirring for a total of 1 hour at ambient temperature, the reaction mixture was applied to a 0.5 mm ×20 cm ×20 cm silica gel TLC plate, the solvents were allowed to evaporate from the plate, and the plate was developed with 15% methanol in chloroform (2×). The appropriate band was removed from the plate, powdered and the semi-purified tracer eluted from the silica gel with methanol. The methanolic solution of the tracer was concentrated to dryness and similarly chromatographed on a 0.25 mm ×20 cm ×20 cm silica gel TLC plate to provide about 200 micrograms (ug) of the purified (XIV), the structure of which is depicted in figure (XIV): MS (FAB) yields MH+@594.

EXAMPLE 6

This example illustrates the preparation of an immunogen of the invention illustrated in formula (XV) in which BSA represents a bovine serum albumin moiety attached through an amide linkage to the remainder of the compound.

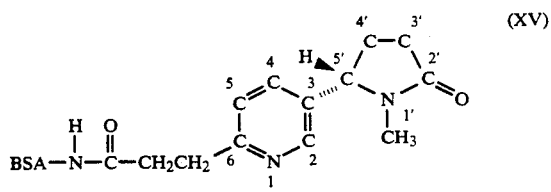
(XV)

23.1 mg of (s)-(—)-6-(2-carboxyethyl) cotinine in water was added to bovine serum albumin (65.2 mg) with stirring. The starting pH was 5.53. 1-ethyl-3-(3-dimethylaminopropyl) carbodiimide (112.5 mg) was added in 2 parts adjusting the pH with 0.01 N HCL and 0.1 N HCl after each addition to about pH 5.5–5.7. The mixture was stirred at 2°–8° C. for 18 hours. The ending pH was 6.6. The mixture was dialyzed against deionized water at room temperature for 2 days with 4 changes of dialysate. The solution from the dialyzing tube was found to contain 11.4 mg/ml protein via the Biuret protein concentration determining method.

EXAMPLE 7

This example illustrates the preparation of a preferred immunogen of the invention illustrated in formula (XVI) in which BSA represents a bovine serum albumin moiety attached through an amide linkage to the remainder of the compound.

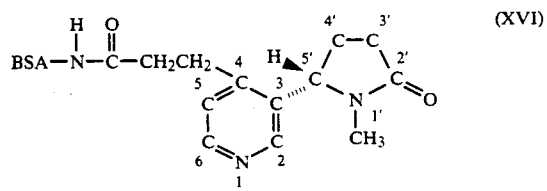
(XVI)

57.4 mg of (s)-(—)-4-(2-carboxyethyl) cotinine in 10 ml deionized water was added to bovine serum albumin (151.58 mg) with stirring. The pH was adjusted to 6.0 with 0.1 N HCl. 1-ethyl-3-(3-dimethylaminopropyl)carbodiimide (250 mg) was added in 5 parts adjusting the pH mixture with 0.1 N HCl after each addition to about pH 6.0. The mixture was stirred for 18 hours. Next, the mixture was dialyzed in a cellulose dialyzing tube (Spectra/Por®, MW 12,000–14,000) against distilled water for 48 hours with 5 changes of dialysate. The solution from the dialyzing tube was found to contain 13.5 mg/ml of protein via the Biuret protein concentration determining method.

EXAMPLE 8

Antisera were generated from the immunogens of Examples 6 and 7 above and were utilized in fluorescence polarization immunoassays (FPIAs) directed to the determination of cotinine in urine samples. The antisera generated from the immunogen of Example 7 was considered to perform better in the FPIA than the antisera generated from the immunogen of Example 6.

The configuration of the preferred reagents, calibrators and controls for the FPIAs is as follows:

1. The tracer formulation is 120 nanomolar tracer in: 0.1 molar tris buffer at pH 7.5, 0.01% bovine gammaglobulin, and 0.1% sodium azide.
2. The antiserum formulation comprises rabbit serum diluted with: 0.1 molar sodium citrate buffer at pH 6.5, 10% glycerol, 2% bovine serum albumin, and 0.1% sodium azide.
3. The pretreatment solution consists of: 0.1 molar tris buffer at pH 7.5, 0.01% bovine gamma-globulin, 0.1% sodium azide and 10 mg/ml riboflavin binding protein.

4. The wash solution consists of: 0.1 molar sodium phosphate buffer at pH 7.5, 0.1% sodium azide and 0.01% bovine gamma-globulin.
5. The dilution buffer comprises: 0.1 molar sodium phosphate buffer at pH 7.5, 0.1% sodium azide and 0.01% bovine gamma-globulin.
6. The calibrator/control diluent comprises: 0.9% sodium chloride at pH 6.5, 0.4% octyl sodium sulfate, and 0.1% sodium azide. This calibrator/control diluent helps to neutralize the urine matrix effect seen with antisera raised against haptens derived from cotinine.
7. Cotinine calibrators comprise cotinine in calibrator/control diluent at concentrations of 0.0, 200.0, 500.0, 1000.0, 2000.0 and 4000.0 nanograms per milliliter.
8. Cotinine controls comprise cotinine in calibrator/control diluent at concentrations of 400.0, 1500.0 and 3000.0 nanograms per milliliters.

The antisera generated from the immunogen of Example 7 improved the performance of the assay with respect to matrix effort with negative urines and cross-reactivities to other nicotine/cotinine metabolites when compared to the assay performed using antisera generated from the immunogen of Example 6. Negative urines could read higher than 200 nanograms/milliliter (ng/ml) (a proposed cutoff of the assay) when analyzed with antisera from the immunogen of Example 6 due to matrix effect. This was reduced to 50 ng/ml with the immunogen from Example 7.

In addition, the cross-reactivity to two other metabolites of nicotine was significantly reduced utilizing the immunogen of Example 7 compared to that of Example 6. Representative data is shown in the following Table 1:

TABLE 1

| Immunogen | Metabolite | Concentration Added (ng/ml) | Concentration Found (ng/ml) | % Cross-Reactivity |
|---|---|---|---|---|
| Example 6 | trans-3'-cotinine | 20,000 | 52.03 | 0.3 |
| Example 6 | cotinine-N-oxide | 10,000 | 1493.45 | 14.9 |
| Example 7 | trans-3'-cotinine | 20,000 | 33.28 | 0.2 |
| Example 7 | cotinine-N-oxide | 10,000 | 88.50 | 0.9 |

TABLE 1-continued

What is claimed is:

1. An optically active compound containing less than or equal to 20 percent by weight of the dextrorotatory enantiomer of said compound based on the sum by weight of dextrorotatory and levorotatory enantiomers of said compound, said optically active compound corresponding to the formula:

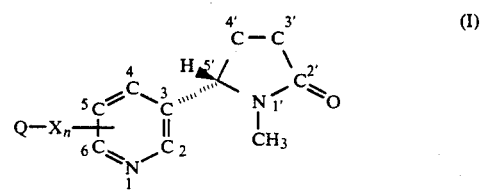

wherein X is a straight or branched chain, saturated divalent radical having 1 to 10 carbon atoms of an ethylenically unsaturated divalent radical having 2 to 10 carbon atoms covalently bonded to the pyridyl ring of said formula (I) at the number 2- 4-, 5- or 6-position of said pyridyl ring, said divalent radical is optionally substituted with 1 or 2 hereto atoms selected from members of the group consisting of S, O and NZ in which Z represents a $C_1$ to $C_3$ allkyl group;

n = 1 or 0; and

Q is a functional group selected from —COOH, —$NH_2$ (provided that n does not equal 0), —C(O)$NHNH_2$, —O(CO)Cl, —CHO, —NCS or —NCO.

2. The optically active compound of claim 1 wherein n=1 and X is bonded to the pyridyl ring of said formula at the number 4-, 5- or 6-position.

3. The compound of claim 1 wherein n=1 and X is a $C_1$ to $C_8$ alkylene group.

4. The compound of claim 1 wherein n=1 and X is —$CH_2CH_2$—.

5. The compound of claim 2 wherein X is —$CH_2CH_2$—.

6. The compound of claim 5 wherein Q is —COOH.

* * * * *

UNITED STATES PATENT AND TRADEMARK OFFICE
CERTIFICATE OF CORRECTION

PATENT NO. : 5,164,504
DATED : November 17, 1992
INVENTOR(S) : John A. Walling, Hsiang-Yun Hu, and Barbara E. Hasz It is certified that error appears in the above-identified patent and that said Letters Patent is hereby corrected as shown below:

In column 2, line 7 delete [51(3),] and insert --41(3),--

In column 2, line 44 delete [ehtylenically] and insert --ethylenically-- before "unsaturated".

In column 6, line 54 delete [t] and insert --three-- before "days".

In column 6, line 55 insert --stimulation by antigen, mature into plasma cells which synthesize-- before "antibody".

In column 12, line 34 delete [ba] and insert --bar-- before "and".

In column 12, line 47 delete [oil] and insert --of-- before "phenyl".

In column 18, line 37 delete the space between 1 N to read --1N--.

In Claim 1, line 35 delete [allkyl] and insert --alkyl-- before "group".

Signed and Sealed this

Thirtieth Day of November, 1993

Attest:

BRUCE LEHMAN

Attesting Officer

Commissioner of Patents and Trademarks